United States Patent
Narula et al.

(10) Patent No.: US 7,504,368 B2
(45) Date of Patent: Mar. 17, 2009

(54) SUBSTITUTED 1-(2-ETHYL-1-METHYL-CYCLOPROPYL)-ONE/OL DERIVATIVES

(75) Inventors: Anubhav P. S. Narula, Hazlet, NJ (US); Edward Mark Arruda, Cliffwood, NJ (US)

(73) Assignee: Internation Flavors & Fragrances Inc., New York, NY (US)

( * ) Notice: Subject to any disclaimer, the term of this patent is extended or adjusted under 35 U.S.C. 154(b) by 0 days.

(21) Appl. No.: 12/038,017

(22) Filed: Feb. 27, 2008

(65) Prior Publication Data

US 2008/0214431 A1    Sep. 4, 2008

Related U.S. Application Data

(62) Division of application No. 11/065,415, filed on Feb. 24, 2005, now Pat. No. 7,410,942.

(51) Int. Cl.
*C11D 3/50* (2006.01)

(52) U.S. Cl. .............................. 510/102; 512/8; 568/700
(58) Field of Classification Search ................. 568/700; 512/8; 510/102
See application file for complete search history.

(56) References Cited

OTHER PUBLICATIONS

M.P. Cooke, Jr., Journal of Organic Chemistry, vol. 44, issue 14, pp. 2461-2468, 1979, no month available.*
M.P. Cooke, Jr., Tetrahedron Letters, issue 15, pp. 1281-1284, 1973, no month available.*

* cited by examiner

*Primary Examiner*—John R Hardee
(74) *Attorney, Agent, or Firm*—Elizabeth M. Quirk; XuFan Tseng; Joseph F. Leightner

(57) ABSTRACT

The present invention is directed to novel ketone and alcohol compounds and the use of these novel compounds in creating fragrances, and scents in items such as perfumes, colognes and personal care products.

7 Claims, No Drawings

SUBSTITUTED 1-(2-ETHYL-1-METHYL-CYCLOPROPYL)-ONE/OL DERIVATIVES

RELATED APPLICATIONS

This application is a divisional of U.S. Ser. No. 11/065,415, filed Feb. 24, 2005, now U.S. Pat. No. 7,410,942, the contents hereby incorporated by reference as if set forth in its entirety.

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons with an ability to create new fragrances for perfumes, colognes and personal care products. Those with skill in the art appreciate how differences in the chemical structure of a molecule can result in significant differences in the odor, notes and characteristics of the molecule. These variations and the ongoing need to discover and use new chemicals in the development of new fragrances allow perfumers to apply new compounds in creating new fragrances.

SUMMARY OF THE INVENTION

The present invention provides novel chemicals, and the use of the chemicals to enhance the fragrance of perfumes, toilet waters, colognes, personal care products and the like. In addition, the present invention is directed to the use of the novel chemicals to modify or enhance the fragrance in perfumes, toilet waters, colognes, personal products and the like.

More specifically, the present invention is directed to the novel compounds, represented by the general structures of Formula I and Formula II set forth below:

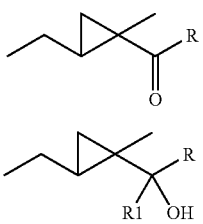

Formula I

Formula II wherein R is a hydrocarbon moiety consisting of 2 to 10 carbon atoms, including cyclopentyl, cyclohexyl, phenyl, benzyl, or phenylethyl. R1 is either hydrogen, methyl or ethyl.

Another embodiment of the invention is a method for enhancing a perfume by incorporating an olfactory acceptable amount of the compounds provided above.

These and other embodiments of the present invention will be apparent by reading the following specification.

DETAILED DESCRIPTION OF THE INVENTION

In Formula I and Formula II above, R represents a hydrocarbon cyclic or aromatic chain, preferably of 2 to 10 carbon atoms in length, most preferably, R is a pentyl group. Hydrocarbon, cyclic or aromatic R groups include, but are not limited to the straight alkyl, cyclic, and aromatic chains. Suitable straight hydrocarbon moieties include ethyl, propyl, butyl, cyclopentyl, cyclohexyl, and the like. Suitable branched hydrocarbon moieties include isopropyl, sec-butyl, tert-butyl, 2-ethyl-propyl, and the like. Suitable hydrocarbon moieties containing double and triple bonds include ethene, propene, 1-butene, 2-butene, penta-1-3-deine, hepta-1,3,5-triene, butyne, hex-1-yne and the like. Suitable aromatic moieties include phenyl, benzyl, phenylethyl and the like.

In Formula II above, R1 represents a hydrogen, a methyl or an ethyl group. Those with skill in the art will recognize that the compound of Formula I of the present invention has a chiral center, thereby providing several isomers of the claimed compound. As used herein the compounds described herein include the isomeric mixtures of the compounds as well as those isomers that may be separated using techniques known to those with skill in the art. Suitable separation techniques include chromatography, particularly gel chromatography.

The compounds of the present invention may be prepared from the following compounds:

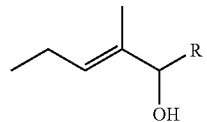

Formula III

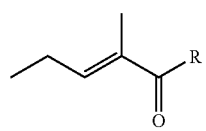

Formula IV wherein R is understood to have the same meaning as set forth above.

The preparation and use of the compound of Formula III is discussed in U.S. Pat. No. 4,585,662, the contents of which are incorporated herein by reference. The compound of Formula IV may be prepared from the compound of Formula III by following the Oppenauer oxidation reaction procedure known to persons skilled in the art.

The compound of Formula I may be prepared from the compound of Formula IV by following the procedure of the Corey cyclopropanation reaction, see Example A below. The compound of Formula II may be prepared from the compound of Formula III by following the procedure of the Simmons-Smith cyclopropanation reaction, see Example B below. The compound of Formula II may also be prepared from the compound of Formula I by following the Red-Al reduction reaction, see Example C below. We have discovered that the compounds have a strong and pleasant fruity note with violet, soft green tones that are well suited for use as a fragrance ingredient.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million and g is understood to be grams.

EXAMPLE A

Preparation of
1-(2-Ethyl-1-Methyl-Cyclopropyl)-Hexane-1-One

To a dry 2 liter multi-neck round bottom flask fitted with an air stirrer, nitrogen inlet condenser and an addition funnel under vacuum 1.5 g of 60% NaH and 50 ml of hexane were added. The mixture was stirred, allowed to settle and hexane removed. The above procedure was repeated twice. The pressure was reduced and the vacuum broken under nitrogen. Fifty (50) ml Dimethylsulfoxide (DMSO) and 9 g of 98% $(CH_3)_3SOI$ were slowly added over 90 minutes. Hydrogen gas began to evolve. The mixture was heated to 70° C. until hydrogen stopped evolving. The mixture was cooled to a room temperature and 4-methyl-3-decene-5-one was added dropwise. Upon completion of the addition of 4-methyl-3-decene-5-one, the mixture was stirred for 2 hours at a room temperature and then for 1 hour at 50° C. The mixture was quenched with 80 ml of water and the organic layer extracted with three portions of 25 ml of $Et_2O$. The extracts were washed again with three portions of 25 ml of cold water and the organic layer then dried over anhydrous $MgSO_4$. The ether was evaporated.

The NMR spectrum of the 1-(2-ethyl-1-methyl-cyclopropyl)-hexane-1-one is as follows: 0.9 ppm (m, 3H); 1.0 ppm (m, 3H); 1.2-1.4 ppm (m, 7H); 1.5-1.7 ppm (m, 3H); 2.0 ppm (m, 2H); 4.0 ppm (t, 1H); 5.4 ppm (t, 1H).

EXAMPLE B

Preparation of
2-Ethyl-1-Methyl-Alpha-Pentyl-Cyclopropanemethanol

To a dry 2 liter multi-neck round bottom flask fitted with an air stirrer, nitrogen inlet condenser and an addition funnel 8 g of a ZnCu and 75 ml of Methyl Tertiary Butyl Ether (MTBE) was added. The resulting mixture was stirred for 5 minutes. After the temperature of the mixture was stabilized, 24 g of $CH_2I_2$ was added over 10 minutes while stirring. After the temperature of the mixture was stabilized, the mixture was heated to reflux. As the temperature of the mixture reached 44° C., 17 g of 4-methyl-3-decene-5-ol was added over 30 minutes. After the addition of 4-methyl-3-decene-5-ol, a first sample was taken. Additional samples were taken every hour for three hours. Then the sample was quenched with saturated $NH_4Cl$, aqueous layer separated and the organic layer filtered through celite. The gas chromatography test indicated that 96.93% of the original alcohol converted to the cyclopropanated alcohol.

The NMR spectrum of the 2-ethyl-1-methyl-alpha-pentyl-cyclopropanemethanol is as follows: 0.0 ppm (m, 1H); 0.5 ppm (m, 2H); 0.88 ppm (d, 3H); 1.0 ppm (m, 6H); 1.2-1.4 ppm (m, 9H); 1.48 ppm (m, 1H); 2.75 ppm (m, 1H).

EXAMPLE C

Preparation of 2-Ethyl-1-Methyl-Alpha-Pentyl-Cyclopropanemethanol from 1-(2-Ethyl-1-Methyl-Cyclopropyl)-Hexane-1-One Approximately 1 g of 1-(2-ethyl-1-methyl-cyclopropyl)-hexane-1-one was added by a pipette into a 13 mm by 100 mm test tube. Red-Al (30% solution in toluene) was added dropwise with shaking until no heat was given off. The mixture was quenched by adding 5% Na$_2$CO$_3$ until foaming stopped. The mixture was shaken and the organic layer was separated. The organic layer was washed with 5 ml of brine. The resulting organic layer was poured onto a watch glass and the solvent was evaporated.

The NMR spectrum of the 2-ethyl-1-methyl-alpha-pentyl-cyclopropanemethanol is as follows: 0.0 ppm (m, 1H); 0.5 ppm (m, 2H); 0.88 ppm (d, 3H); 1.0 ppm (m, 6H); 1.2-1.4 ppm (m, 9H); 1.48 ppm (m, 1H); 2.75 ppm (m, 1H).

EXAMPLE D

Preparation of
2-Ethyl-Alpha,1-Dimethyl-Alpha-Pentyl Cyclopropanemethanol

To a dry 5 liter multi-neck round bottom flask fitted with an air stirrer, nitrogen inlet condenser and an addition funnel 1,617 g of CH$_3$Li was added and stirred. Three hundred and thirty six (336) g of 1-(2-ethyl-1-methyl-cyclopropyl)-1-hexanone (see Example A for the preparation of 1-(2-ethyl-1-methyl-cyclopropyl)-1-hexanone) was added dropwise over 105 minutes. The temperature of the reaction rose to 63° C. The reaction mixture was aged for 150 minutes and a first sample was taken at 37° C. A second sample was taken at 30° C. after 30 minutes. The mixture was quenched with acetic acid, allowed to settle and layers separated. The aqueous layer was washed twice with 100 ml of toluene. The toluene extracts were added to the organic layer and washed with Na$_2$CO$_3$.

The NMR spectrum of the 2-ethyl-alpha,1-dimethyl-alpha-pentyl cyclopropanemethanol is as follows: −0.18 ppm (d, 1H); −0.25 ppm (d, 1H); 0.65 ppm (m, 1H); 1.1 ppm (s, 3H); 1.18 ppm (s, 3H); 1.55 ppm (m, 2H); 1.25-1.5 ppm (m, 8H).

What is claimed is:

1. A method of improving, enhancing or modifying a fragrance formulation through the addition of an olfactory acceptable amount of a compound of formula:

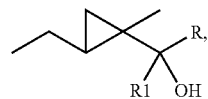

wherein R is a hydrocarbon chain consisting of 2 to 10 carbon atoms and R1 is selected from the group consisting of hydrogen, methyl, and ethyl.

2. The method of claim 1, wherein the fragrance formulation is incorporated into a product selected from the group consisting of a perfume, a cologne, a toilet water, a cosmetic product, a personal care product, a fabric care product, a cleaning product, and an air freshener.

3. The method of claim 2, wherein the cleaning product is selected from the group consisting of a detergent, a dishwashing composition, a scrubbing compound, and a window cleaner.

4. The method of claim 1, wherein the olfactory acceptable amount is from about 0.005 to about 10 weight percent.

5. The method of claim 1, wherein the olfactory acceptable amount is from about 0.5 to about 8 weight percent.

6. The method of claim 1, wherein the olfactory acceptable amount is from about 1 to about 7 weight percent.

7. A method of improving, enhancing or modifying a fragrance formulation through the addition of an olfactory acceptable amount of a compound of formula:

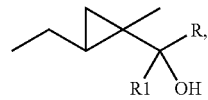

wherein R is a hydrocarbon selected from the group consisting of pentyl, cyclopentyl, cyclohexyl, phenyl, benzyl, and phenyethyl, and R1 is selected from the group consisting of hydrogen, methyl, and ethyl.

* * * * *